US010639257B2

(12) United States Patent
Consoli et al.

(10) Patent No.: US 10,639,257 B2
(45) Date of Patent: May 5, 2020

(54) COMPOSITION FOR COLOURING KERATIN FIBRES

(71) Applicant: Beauty & Business S.p.A., Milan (IT)

(72) Inventors: Antonio Consoli, Urgnano (IT); Massimo Fabbi, Mozzo (IT); Katiuscia Grevalcuore, Bergamo (IT)

(73) Assignee: Beauty & Business S.p.A., Milan (IT)

( * ) Notice: Subject to any disclaimer, the term of this patent is extended or adjusted under 35 U.S.C. 154(b) by 0 days.

(21) Appl. No.: 16/163,081

(22) Filed: Oct. 17, 2018

(65) Prior Publication Data
US 2019/0117541 A1 Apr. 25, 2019

(30) Foreign Application Priority Data
Oct. 19, 2017 (IT) .......... 102017000118597

(51) Int. Cl.
A61Q 5/10 (2006.01)
A61K 8/44 (2006.01)
A61K 8/37 (2006.01)
A61K 8/86 (2006.01)
A61K 8/22 (2006.01)
A61K 8/49 (2006.01)
A61K 8/39 (2006.01)

(52) U.S. Cl.
CPC .......... A61K 8/44 (2013.01); A61K 8/22 (2013.01); A61K 8/37 (2013.01); A61K 8/39 (2013.01); A61K 8/4913 (2013.01); A61K 8/86 (2013.01); A61Q 5/10 (2013.01); A61K 2800/30 (2013.01); A61K 2800/4324 (2013.01); A61K 2800/48 (2013.01); A61K 2800/524 (2013.01); A61K 2800/882 (2013.01)

(58) Field of Classification Search
CPC ........ A61Q 5/10; A61K 8/411; A61K 8/4926; A61K 8/415; A61K 8/22; A61K 2800/88; A61K 2800/882; A61K 8/37; A61K 8/062; A61K 2800/48; A61K 8/064; A61K 8/85; A61K 2800/524; A61K 31/198
See application file for complete search history.

(56) References Cited

U.S. PATENT DOCUMENTS 3,997,659 A 12/1976 Knohl et al.

FOREIGN PATENT DOCUMENTS

EP 2110117 A1 10/2009
WO 2006106390 A2 10/2006
WO WO 2006/106390 A2 * 10/2006 ............ A61Q 5/10

OTHER PUBLICATIONS

Mitchell, Italian Search Report for IT 201700118597 dated Apr. 27, 2018.

* cited by examiner

Primary Examiner — Eisa B Elhilo
(74) Attorney, Agent, or Firm — Greer, Burns & Crain, Ltd.; Gregory P. Einhorn

(57) ABSTRACT

The present invention refers to a hair dye comprising a) an alkalinising agent consisting of at least one amino acid having a pKa of greater than 10.00 and at least one ester of a fatty acid and glycerol polyethoxylate; and b) at least one oxidation colourant. In particular, the composition of the invention does not comprise any further alkalinizing agent. Kits and methods for colouring hair based on this composition also fall within the scope of this invention.

21 Claims, 1 Drawing Sheet

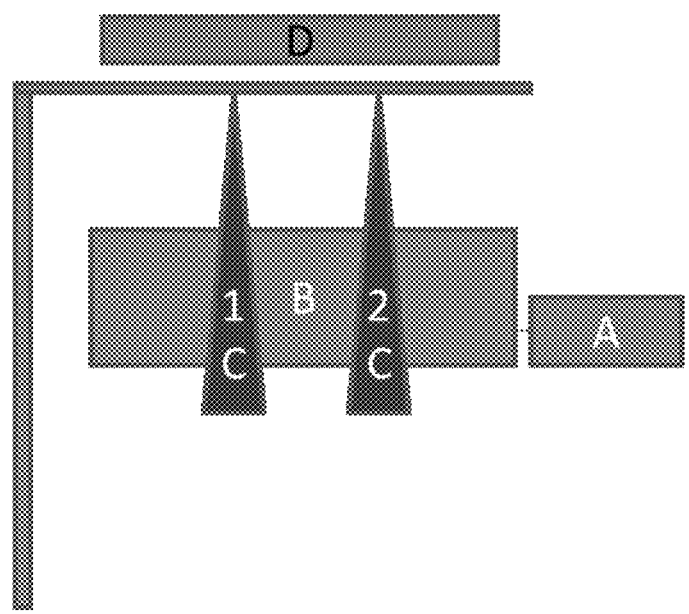

COMPOSITION FOR COLOURING KERATIN FIBRES

This application is a U.S. utility patent application claiming benefit of priority to Italian patent application number 102017000118597, filed Oct. 19, 2017. The aforementioned application is expressly incorporated herein by reference in its entirety and for all purposes.

FIELD OF THE INVENTION

The present invention refers to the cosmetic field, in particular to the hair-dyeing field.

STATE OF THE ART

In the past, hair was dyed mainly to cover areas of grey hair; today there is an increased demand to have a fashionable hair colour which expresses one's personality.

Oxidative dyes have become of substantial importance in the hair-dye sector. The dye is created by the reaction of primary intermediaries and couplers in the presence of an oxidizer, in such a manner to produce a vast range of colour shades. The dyes obtained in this manner must fulfil high-level requisites in terms of resistance to washing, to sunlight, to sweat, to perm treatments, to acids, to bases and abrasion. They are generally stable from four to six weeks under normal conditions and are therefore called "permanent" for this reason.

The oxidation system is based upon the reaction of the so-called primary intermediaries with couplers; both types of molecules are colourless. In the presence of air or oxidizers such as hydrogen peroxide, the primary colourants, which are primary aromatic amines with a hydroxyl or an additional, substituted or unsubstituted, amino group, in para or ortho position, react with couplers that are of the resorcinol or m-aminophenol, m-phenylenediamine or 1-naphthol type.

Given that the dimension of the dye molecules that are thus formed inside the cuticle is greater than the dimension of the initial primary intermediates and of the highly-diffusible couplers, they remain trapped and this is why there is no significant fading with the subsequent washes or due to the action of external agents.

In order to colour, the oxidation dyes also require the presence of an alkalinizing agent.

Ammonia is historically the most used alkalinizing agent. This compound has a characteristic odour and many users perceive it as being unpleasant.

In the last twenty years, ammonia-free dyes containing alkanolamines have spread on the market and monoethanolamine (MEA) is the most widely used example. Alkanolamines have been documented in literature as being particularly aggressive for hair fibres, as they tend to damage the hair structure, with the consequent loss of shine, combability and elasticity (Comparison of damage to human hair fibers caused by monoethanolamine- and ammonia-based hair colorants, J. Cosmet. Sci., 65, 1-9; Patent WO2017109132 by L'Oreal).

The purpose of this invention is to develop a composition for colouring keratin, in particular hair, which does not have an unpleasant odour, which has a high degree of durability to washing and resistance to fading caused by sunlight, but without damaging the hair fibre and rather guaranteeing excellent results in terms of shine, combability and elasticity.

In particular, there is the need for a composition in which the alkalinizing agent does not present the disadvantages of the alkalinizing agents that are commonly used in the field. In the field, there are various patent documents that describe hair dyes wherein the alkalinizing agent is typically ammonia or an alkanolamine, in particular, monoethanolamine. For example, WO2017085117, DE102015218077, U.S. Pat. Nos. 8,257,447, 8,241,370, 8,343,237, WO2016016148, US20100175706, WO2010130490, EP2198834, EP2198842, EP2198843, EP2143419, DE102005062830.

Some of these documents also mention arginine or other basic amino acids in their compositions, generally as a basifying adjuvant or as having a restructuring action.

SUMMARY OF THE INVENTION

It is an object of the present invention a composition for colouring keratin fibres, in particular, human hair, comprising:
- an alkalinising agent consisting of at least one amino acid having a pKa of greater than 10.00 and at least one ester of a fatty acid and glycerol polyethoxylate;
- at least one oxidation colourant, wherein said composition does not contain further alkalinising agents, such as, for example, ammonia and alkanolamines.

Said composition, optionally mixed and opportunely diluted with an activator, colours hair in a permanent manner, which is therefore stable over time and long-lasting as regards washing and sunlight exposure, it does not have an unpleasant odour, does not damage hair, and, surprisingly, provides it with shine, manageability and elasticity.

In particular, the use of the combination of amino acid, for example arginine, and ester of a fatty acid with glycerol polyethoxylate as the sole alkalizer, and the absence of further alkalinizing agents such as ammonia and alkanolamine avoids the problems of the prior art mentioned above, obtaining at the same time the effects of a permanent and resistant dye.

Moreover, a synergistic effect of the amino acid with the ester of a fatty acid with glycerol polyethoxylate has been found on the shine, manageability and elasticity of the hair, which, as well as not showing any weakening, on the contrary presents the aforementioned characteristics improved.

The use of a composition comprising at least one amino acid having a pKa of greater than 10.00 and at least one ester of a fatty acid with glycerol polyethoxylate as alkalizing agent is also an object of the present invention.

Kits for dyeing and hair-colouring methods based on the composition of the invention also fall within the scope of this invention.

DETAILED DESCRIPTION OF THE INVENTION

Definitions

In the context of this invention, "elasticity" means the measurement of the rigidity of the keratin fibre. It is a mechanical property defined by the relationship between the applied force and the lengthening of the fibre itself. "Tensile strength" is also used here as a synonym of elasticity.

In the context of this invention, "alkalinizing agent" or "alkalizer" means an ingredient or a combination of ingredients capable of raising the pH of the cosmetic composition above 7. In the context of this invention, "neutralising agent" or "neutralising element" means an ingredient capable of raising the pH of the composition from a value below 7 to neutral pH. In the context of this invention, "activator" means an agent capable of favouring the oxidation and coupling reaction between primary colourants and couplers.

FIGURES

FIG. 1. Structure used to assess dynamic shine.

The composition of the invention may be in the form of an O/W (oil in water) or W/O (water-in-oil) emulsion, a liquid, biphasic liquid, gel, oil, aerosol, mousse.

The composition of the invention may optionally be in a "ready to use" form, comprising two or more components to be mixed prior to use. Alternatively, it can be applied directly to the hair and, in such a case, the oxygen present in the air is the activator.

The amino acid having a pKa of greater than 10.00 may be any amino acid known in the sector having a pKa of greater than 10.00, it can be in levo or dextro form.

Amongst the amino acids having a pKa of greater than 10.00 that characterise the invention, there are: arginine, lysine, tyrosine, proline and cysteine. Arginine and lysine are the preferred amino acids, in particular the L-arginine obtained from the fermentation of plant sources of carbohydrates. The latter is therefore particularly preferred as it is an alkalinizing agent of natural origin. The quantity of amino acid may typically vary between 0.1 and 20 wt. %, preferably between 0.2 and 10 wt. %, in proportion to the total weight of the composition.

Amongst the esters of fatty acids with glycerol polyethoxylate, the preferred compounds are those having an average ethoxylation number between 5 and 200 and the esterification is carried out with fatty acids which may be saturated, unsaturated or branched, with a number of carbons preferably comprised between 8 and 22. On the basis of the moles that have reacted, the fatty acids can form monoesters, diesters or triesters. The quantity of the aforementioned ester may typically vary between 0.05 and 10 wt. %, preferably between 0.1 and 5 wt. %, in relation to the total weight of the composition.

The following are non-exhaustive examples of esters of fatty acids with glycerol polyethoxylate to be used in this invention: Peg-90 glyceryl isostearate, Peg-30 glyceryl triisostearate, Peg-9 glyceryl laurate, Peg-8 glyceryl trilaurate. The preferred esters are Peg-90 glyceryl isostearate and Peg-30 glyceryl triisostearate. The names reported in this invention follow the International Nomenclature of Cosmetic Ingredients (IND). Certain commercial names are OXETAL VD 92, marketed by ZSCHIMMER SCHWARZ and EMALEX GWIS-340, marketed by Nihon Emulsion Co. LTD.

In a preferred embodiment of the invention, said amino acid is arginine and said ester is PEG-90 glyceryl isostearate.

In another preferred embodiment, said amino acid is lysine and said ester is PEG-30 glyceryl triisostearate.

The composition which is the subject matter of the invention must also comprise at least one oxidation colourant, preferably selected amongst: 1-acetoxy-2-methylnaphthalene, 5-amino-4-chloro-o-cresol, 4-amino-m-cresol, 6-amino-m-cresol, 3-amino-2,4-dichlorophenol, 6-amino-2,4-dichloro-m-cresol, 3-amino-2,4-dichlorophenol, 5-amino-2,6-dimethoxy-3-hydroxypyridine, 5-amino-2,6-dimethoxy-3-hydroxypyridine, 3-amino-2,6-dimethylphenol, 2-amino-5-ethylphenol, 5-amino-4-fluoro-2-methylphenol sulphate, 2-amino-4-hydroxyethylaminoanisole, 2-amino-4-hydroxyethylaminoanisole, 2-amino-3-hydroxypyridine, 4-amino-2-hydroxytoluene, 2-aminomethyl-p-aminophenol, 4-amino-2-nitrodiphenylamine-2'-carboxylic acid, m-aminophenol, o-Aminophenol, p-aminophenol, 1,3-bis-(2,4-diaminophenoxy)propane, 4,6-bis(2-hydroxyethoxy)-m-phenylenediamine, 2,6-bis(2-hydroxyethoxy)-3,5-pyridinediamine, N,N-bis(2-hydroxyethyl)-p-phenylenediamine, 4-chloro-2-aminophenol, 2-chloro-p-phenylenediamine, 4-chlororesorcinol, N-cyclopentyl-m-aminophenol, 3,4-diaminobenzoic acid, 4,5-diamino-1-((4-chlorophenyl)methyl)-1H-pyrazole-sulphate, 2,3-diaminodihydropyrazolo pyrazolone dimethosulphonate, 2,4-diaminodiphenylamine, 4,4'-diaminodiphenylamine, 2,4-diamino-5-methylphenetole, 2,4-diamino-5-methylphenoxyethanol, 4,5-diamino-1-methylpyrazole, 2,4-diaminophenol 2,4-diaminophenoxyethanol, 2,6-diaminopyridine, 2,6-diamino-3-((pyridin-3-yl)azo)pyridine, N,N-diethyl-m-aminophenol, N,N-diethyl-p-phenylenediamine, N,N-diethyltoluene-2,5-diamine, 2,6-dihydroxy-3,4-dimethylpyridine, 2,6-dihydroxyethylaminotoluene, dihydroxyindole, dihydroxyindoline, 2,6-dimethoxy-3,5-pyridinediamine, m-dimethylaminophenyl urea, N,N-dimethyl-p-phenylenediamine, 2,6-dimethyl-p-phenylenediamine, N,N-dimethyl 2,6-pyridinediamine, 4-ethoxy-m-phenylenediamine, 3-ethylamino-p-cresol, 4-fluoro-6-methyl-m-phenylenediamine, 1-hexyl 4,5-diamino pyrazole sulphate, hydroquinone, hydroxyanthraquinoneaminopropyl methyl morpholinium methosulphate, hydroxybenzomorpholine, hydroxyethoxy aminopyrazolopyridine, hydroxyethylaminomethyl-p-aminophenol, 1-hydroxyethyl 4,5-diamino pyrazole, hydroxyethyl-2,6-dinitro-p-anisidine, hydroxyethyl-3,4-methylenedioxyaniline, hydroxyethyl-p-phenylenediamine, 2-hydroxyethyl picramic acid, 6-hydroxyindole, hydroxypropyl bis(N-hydroxyethyl-p-phenylenediamine), hydroxypropyl-p-phenylenediamine, hydroxypyridinone, isatin, N-isopropyl 4,5-diamino pyrazole, N-methoxyethyl-p-phenylenediamine, 6-methoxy-2-methylamino-3-aminopyridine, 2-methoxymethyl-p-aminophenol, 2-methoxymethyl-p-phenylenediamine, 2-methoxy-p-phenylenediamine, 6-methoxy-2,3-pyridinediamine, 4-methoxytoluene-2,5-diamine, p-methylaminophenol, 4-methylbenzyl 4,5-diamino pyrazole, 2,2'-methylenebis 4-aminophenol, 3,4-methylenedioxyaniline, 3,4-methylenedioxyphenol, 2-methyl-5-hydroxyethylaminophenol, methylimidazoliumpropyl p-phenylenediamine, 2-methyl-1-naphthol, 2-methylresorcinol, 1,5-naphthalenediol, 1,7-naphthalenediol, 2,3-naphthalenediol, 2,7-naphthalenediol, 1-naphthol, 2-naphthol, PEG-3 2,2'-di-p-phenylenediamine, p-phenetidine, m-phenylenediamine, p-phenylenediamine, phenyl methyl pyrazolone, N-phenyl-p-phenylenediamine, picramic acid, pyrocatechol, pyrogallol, resorcinol, sodium picramate, tetraaminopyrimidine, tetrahydro-6-nitroquinoxaline, tetrahydropyranyl, resorcinol, toluene-2,5-diamine, toluene-2,6-diamine, toluene-3,4-diamine, 2,5,6-triamino-4-pyrimidinol, 1,2,4-trihydroxybenzene. The oxidation dyes may be in the form of salts. The total quantity of the combination of the primary colourants and of the couplers in the dye according to the invention preferably varies between approximately 0.001 and 20 wt. %, more preferably between approximately 0.002 and 10 wt. % and even more preferably between approximately 0.01 and 6.0 wt. %.

As stated, the dye which is the subject matter of the invention may be directly applied on the hair and can therefore colour thanks to the presence of the oxygen in the air or it may be mixed with an activator. Activator means, for example, hydrogen peroxide, carbamide peroxide, perborates and persulphates or peracids. Hydrogen peroxide is the preferred compound. The quantity of activator, if present, may vary between 0.1 and 50 wt. % in relation to the ready-to-use mixture.

When the dye is mixed with the activator, which is an acid (pH between approximately 2 and 6.5) in most cases, the pH of the ready-to-use dyes of the invention takes on a value that is determined by the quantity of alkalis in the dye and by the quantity of acid in the oxidizer, as well as by the mixing ratio. Depending on the composition, the ready-to-use dyes obtained in this manner may be slightly acid, neutral or alkaline and have a pH between approximately 3 and 11, preferably between 6.5 and 11.

The dye may also contain a neutralising element such as, for example, sodium hydroxide, potassium hydroxide, urea, allantoin, tripotassium phosphate, sodium saccharin or their combinations, in such quantities to obtain the neutralisation of the acid ingredients that are present in the formulation.

The dyes of the invention may also contain one or more additives, whether natural or synthetic, which are commonly used in the cosmetic sector in solutions, creams, emulsions, gels, aerosols, foams, powders and granulates. Examples of these are solvents such as: water, aliphatic mono or polyalcohols with low molecular weight, their esters and ethers, for example alkanols, in particular having from 1 to 4 carbon atoms, such as ethanol, n-propanol, isopropanol, butanol, isobutanol; bivalent or trivalent alcohols, in particular having from 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerol, diethylene glycol, dipropylene glycol, polyalkylene glycols, such as triethylene glycol, polyethylene glycol, tripropylene glycol and polypropylene glycol; low molecular weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular with between 3 and 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropyl ether; esters such as ethyl formate, methyl formate, methyl acetate, ethyl acetate, propyl acetate, butyl acetate, phenyl acetate, ethylene glycol monoethyl ether acetate or acetic acid hydroxy ethyl ester; amides such as n-methyl-pyrrolidone; as well as urea, tetramethylurea and thiodiglycol. Emulsifiers, chosen amongst anionic, cationic, non-ionic, amphoteric or zwitterionic ones; wetting agents; surfactants, such as fatty alcohol sulphates, alkyl sulphonates, alkylbenzene sulphonates, alkyl trimethyl ammonium salts, alkyl betaines, α-olefin sulphonates, ethoxylated fatty alcohols, nonylphenol ethoxylates, fatty acid alkanolamines, ethoxylated fatty acid esters, polyglycol ether sulphates of fatty acids, alkyl polyglucosides; thickeners, such as higher fatty alcohol, amides, cellulose derivatives, vaseline, paraffin oil, fatty acids and other fatty components in emulsified form, water-soluble polymeric thickeners, for example natural gums, guar gum, xanthan gum, carob flour, pectin, dextran, agar-agar, amylose, amylopectin, dextrin, clays or synthetic hydrocolloids, such as polyvinyl alcohol; conditioning agents, such as lanolin derivatives, cholesterol, pantothenic acid, cationic water-soluble polymers, protein derivatives, provitamins, vitamins, plant extracts, sugar and betaine; auxiliary agents, such as electrolytes, antioxidants, fatty amides, sequestrants, film-forming agents and preservatives as well as beeswax, may also be present.

The addition of surfactants or non-ionic and/or anionic emulsifiers in the dyes of this invention may be particularly advantageous, such as, for example, fatty alcohol sulphates, in particular lauryl sulphate, sodium cocoyl sulphate; ethoxylated fatty alcohol sulphates, in particular, sodium lauryl ether sulphates with from 2 to 4 molecular units of ethylene oxide, ethoxylated fatty acid esters, ethoxylates nonylphenol, ethoxylated fatty alcohols, alkylbenzene sulphonates or fatty acid alkanolamides, preferably in a total quantity of between 0.1 and 30 wt. %, more preferably between 0.2 and 15 wt. %.

Examples of useful cationic surfactants consist of quaternary ammonium compounds; ammonium halides such as alkyl trimethyl ammonium chlorides, dialkyl dimethyl ammonium chlorides and trialkyl methyl ammonium chlorides. Specific examples are cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other useful cationic surfactants are quaternised protein hydrolysates.

In addition to non-ionic organic thickeners with properties similar to wax and to non-ionic surfactants, the dye may include the customary cosmetic cationic resins. The following are particularly preferred: Polyquaternium-6 (poly(dimethyl-diallyl ammonium chloride)), Polyquaternium-7 (diethyl-diallyl ammonium chloride/acrylamide copolymer), Polyquaternium-10 (cationic cellulose), Polyquaternium-11 (diethyl sulphate of the N,N-dimethyl-aminoethyl methacrylate/PVP acid copolymer), Polyquaternium-22, Polyquaternium-35 and Polyquaternium-37 (trimethyl-aminoethyl methacrylate chloride polymer), alone or in their mixtures. The total quantity of these cationic resins in the dye may be between approximately 0.1 and 6 wt. %.

The composition which is the subject matter of the invention may be obtained, as an example, by means of the following production protocol. In a first phase, the fatty components, also including a component that is part of the family of the fatty acid esters with glycerol polyethoxylate, are weighed and heated until fusion. The second phase contains the colourants, salts such as, for example, sodium sulphite and isoascorbic acid, water and suitable solvents. These salts, in order to be dissolved or to not break down, typically require a pH of 7. In order to bring the pH to 7, a neutralising element is generally used, such as, for example, potassium or sodium hydroxide. Subsequently, phase 1 is joined with phase 2 to create the emulsion and an amino acid having a pKa greater than 10.00 is added to provide the composition with the necessary basicity. Any fragrances or active elements may be added during the cooling stage.

The composition which is the subject matter of the invention may be applied on hair, for example, as per the following methods:

1—The composition is mixed with an activator immediately prior to dyeing the hair and then a sufficient quantity of the ready-to-use colouring mixture is applied on the hair, generally between approximately 60 and 200 grams on the basis of the hair thickness and quantity.

The mixture is left on the hair for between 5 and 60 minutes at a temperature between 5 and 50° C., preferably for 35 minutes at 30° C.; subsequently, the hair is rinsed with water and dried. If necessary, the hair is washed with a shampoo after it has been rinsed and it is optionally rinsed one more time with a mild organic acid, for example, an aqueous solution of tartaric acid. The hair is then dried.

2—The dye is directly applied on the hair and is left on for between 5 and 60 minutes at a temperature between 5 and 50° C., preferably for 35 minutes at 30° C.; subsequently the hair is rinsed with water and dried. The dye can be applied for multiple consecutive days until the desired colour intensity is achieved. In this case, the oxygen in the environmental air works as an activator (progressive dye).

3—The dye is applied directly on the hair and subsequently dried without rinsing. The dye can be applied for multiple consecutive days until the desired colour intensity is achieved. Here too, the oxygen in the environmental air works as an activator (progressive dye).

It has also been found that the composition according to the invention may be advantageously used in the progressive dye because it is capable of providing darker colours with each subsequent application, when compared to traditional progressive dyes, therefore requiring fewer applications to reach the desired colour (see example 6).

Moreover, it has also been found that the composition according to the invention has greater viscosity when compared to traditional dyes, thus indicating that it is advantageously less likely to drip, for example, from the brush during the transfer of the mixture from the bowl to the hair, and will hold better on the head during the developing time of the dye (see example 7).

The following examples will further illustrate the invention.

EXAMPLES

The components shown in the examples are named in accordance with INCI nomenclature (Decision of the European Community 2006/257/EC and subsequent amendments—International nomenclature cosmetic ingredient).

Table 1 shows the formula of the activators used for the examples below. Formulas F1, F2, F3 and F4 represent the various strengths of the activators.

Tables 2, 3 and 4 show the dye formulas used in the subsequent examples. F5*, F8*, F13* and F14* are formulas in conformity with the invention.

TABLE 1

| Activators | | | | |
|---|---|---|---|---|
| COMPONENTS | F1 % | F2 % | F3 % | F4 % |
| AQUA (WATER) | qs 100 | qs 100 | qs 100 | qs 100 |
| HYDROGEN PEROXIDE | 12 | 9 | 6 | 3 |
| CETEARYL ALCOHOL | 3 | 3 | 3 | 3 |
| CETEARETH-20 | 0.6 | 0.6 | 0.6 | 0.6 |
| PHOSPHORIC ACID | 0.1 | 0.1 | 0.1 | 0.1 |
| SODIUM STANNATE | 0.2 | 0.2 | 0.2 | 0.2 |
| SODIUM LAURETH SULPHATE | 0.1 | 0.1 | 0.1 | 0.1 |
| PROPYLENE GLYCOL | 0.1 | 0.1 | 0.1 | 0.1 |
| DISODIUM PYROPHOSPHATE | 0 | 0 | 0 | 0 |
| DIMETHICONE | 0.1 | 0.1 | 0.1 | 0.1 |
| PEG-40 CASTOR OIL | 0.1 | 0.1 | 0.1 | 0.1 |
| PENTASODIUM PENTETATE | 0.1 | 0.1 | 0.1 | 0.1 |
| ETIDRONIC ACID | 0.1 | 0.1 | 0.1 | 0.1 |
| C12-13 ALKYL LACTATE | 1 | 1 | 1 | 1 |

TABLE 2

| Dyes | | | |
|---|---|---|---|
|  | F5* | F6 | F7 |
| AQUA (WATER) | qs 100 | qs 100 | qs 100 |
| ALCOHOL DENAT. | 12 | 12 | 12 |
| OLEIC ACID | 12 | 12 | 12 |
| PROPYLENE GLYCOL | 10 | 10 | 10 |
| LAURETH-2 | 8 | 8 | 8 |
| LAURETH-3 | 4 | 4 | 4 |
| OLEYL ALCOHOL | 3.5 | 3.5 | 3.5 |
| ARGININE | 5 | 5 | — |
| ETHANOLAMINE | — | — | 5 |
| SODIUM LAURETH SULPHATE | 3 | 3 | 3 |
| POTASSIUM HYDROXIDE | 2 | 2 | 2 |
| PEG-90 GLYCERYL ISOSTEARATE | 1 | — | — |
| PARFUM (FRAGRANCE) | 0.7 | 0.7 | 0.7 |
| CETRIMONIUM CHLORIDE | 0.5 | 0.5 | 0.5 |
| P-PHENYLENEDIAMINE | 0.4 | 0.4 | 0.4 |
| ERYTHORBIC ACID | 0.4 | 0.4 | 0.4 |
| SODIUM SULPHITE | 0.4 | 0.4 | 0.4 |
| EDTA | 0.3 | 0.3 | 0.3 |
| RESORCINOL | 0.3 | 0.3 | 0.3 |
| 2-METHYLRESORCINOL | 0.126 | 0.126 | 0.126 |
| M-AMINOPHENOL | 0.076 | 0.076 | 0.076 |
| P-AMINOPHENOL | 0.0668 | 0.0668 | 0.0668 |
| 2,4-DIAMINOPHENOXYETHANOL HCL | 0.018 | 0.018 | 0.018 |

TABLE 3

| Dyes | | | | | | |
|---|---|---|---|---|---|---|
|  | F8* | F9 | F10 | F11 | F12 | F13* |
| AQUA (WATER) | qs100 | qs100 | qs100 | qs100 | qs100 | qs100 |
| CETEARYL ALCOHOL | 20 | 20 | 20 | 20 | 20 | 20 |
| ARGININE | 9 | 9 | — | — | — | — |
| LYSINE | — | — | — | — | — | 9 |
| PEG-90 GLYCERYL ISOSTEARATE | 2 | — | — | 2 | — | — |
| ETHANOLAMINE | — | — | 9 | 9 | — | — |
| PEG-30 GLYCERYL TRIISOSTEARATE | — | — | — | — | — | 2 |
| AMMONIA | — | — | — | — | 5 | — |
| LAURETH-3 | 3 | 3 | 3 | 3 | 3 | 3 |
| TOLUENE-2,5-DIAMINE SULPHATE | 1.668 | 1.668 | 1.668 | 1.668 | 1.668 | 1.668 |
| SODIUM LAURETH SULPHATE | 1.65 | 1.65 | 1.65 | 1.65 | 1.65 | 1.65 |
| OLETH-5 PHOSPHATE | 1.02 | 1.02 | 1.02 | 1.02 | 1.02 | 1.02 |
| DIOLEYL PHOSPHATE | 0.98 | 0.98 | 0.98 | 0.98 | 0.98 | 0.98 |
| SODIUM LAURYL SULPHATE | 0.9 | 0.9 | 0.9 | 0.9 | 0.9 | 0.9 |
| GLYCERYL STEARATE SE | 0.75 | 0.75 | 0.75 | 0.75 | 0.75 | 0.75 |

TABLE 3-continued

| | Dyes | | | | | |
|---|---|---|---|---|---|---|
| | F8* | F9 | F10 | F11 | F12 | F13* |
| PARFUM (FRAGRANCE) | 0.6 | 0.6 | 0.6 | 0.6 | 0.6 | 0.6 |
| CERA ALBA (BEESWAX) | 0.5 | 0.5 | 0.5 | 0.5 | 0.5 | 0.5 |
| SODIUM SULPHATE | 0.5 | 0.5 | 0.5 | 0.5 | 0.5 | 0.5 |
| SODIUM SULPHITE | 0.5 | 0.5 | 0.5 | 0.5 | 0.5 | 0.5 |
| 2-METHYLRESORCINOL | 0.444 | 0.444 | 0.444 | 0.444 | 0.444 | 0.444 |
| EDTA | 0.3 | 0.3 | 0.3 | 0.3 | 0.3 | 0.3 |
| RESORCINOL | 0.2836 | 0.2836 | 0.2836 | 0.2836 | 0.2836 | 0.2836 |
| ERYTHORBIC ACID | 0.2 | 0.2 | 0.2 | 0.2 | 0.2 | 0.2 |
| LIMNANTHES ALBA SEED OIL (LIMNANTHES ALBA (MEADOWFOAM) SEED OIL) | 0.2 | 0.2 | 0.2 | 0.2 | 0.2 | 0.2 |
| M-AMINOPHENOL | 0.15 | 0.15 | 0.15 | 0.15 | 0.15 | 0.15 |
| 2,4-DIAMINOPHENOXYETHANOL HCL | 0.011 | 0.011 | 0.011 | 0.011 | 0.011 | 0.011 |

TABLE 4

Dye according to the invention, in gel form.

| INGREDIENTS (INCI) | Composition F14* |
|---|---|
| AQUA | Ad 100 |
| PROPYLENE GLYCOL | 7 |
| HYDROXYETHYLCELLULOSE | 2 |
| SODIUM POLYACRYLATE | — |
| CARBOMER | 1 |
| ACRYLATES/METHACRYLAMIDE COPOLYMER | 0.3 |
| PEG-90 GLYCERYL ISOSTEARATE | 1 |
| ARGININE | 9 |
| SODIUM HYDROXIDE | 1 |
| PARFUM (FRAGRANCE) | 0.6 |
| SODIUM SULPHITE | 0.5 |
| ERYTHORBIC ACID | 0.3 |
| EDTA | 0.2 |
| TOLUENE-2,5-DIAMINE SULPHATE | 2.14 |
| 4-CHLORORESORCINOL | 1.367 |
| P-AMINOPHENOL | 0.736 |
| M-AMINOPHENOL | 0.701 |
| 2,4-DIAMINOPHENOXYETHANOL HCL | 0.074 |
| 2-AMINO-3-HYDROXYPYRIDINE | 0.031 |

Production Method of the Dyes According to the Invention

In the first phase, the fatty components, which also comprise a component that belongs to the family of the fatty acid esters with the glycerol polyethoxylate, are weighed and heated until fused. The second phase consists of the colourants, the salts such as sodium sulphite and isoascorbic acid, water and solvents. These salts require a pH of 7 in order to be dissolved or to not be broken down. A neutralising element, such as potassium or sodium hydroxide, is used to bring the pH to 7.

Subsequently, phase 1 is joined with phase 2 to create the emulsion and an amino acid having a pKa greater than 10.00 is added to provide the composition with the necessary basicity. Eventual fragrances or active elements may be added during the cooling stage.

Example 1

Dynamic Shine Test.

The shine has been assessed using a new method that we will call "Dynamic Shine". Unlike the "static" method, like that of the Samba Hair System of Bossanova Technologies, this method allows the shine to be assessed from the roots to the tips thanks to movement. This method has been studied and perfected at Beauty & Business SpA. The method consists in hanging the hair strands (C1 and C2) on a support as shown in FIG. 1. Support B is placed on the back side parallel to the strands. Support B is connected to the motor A which is capable of rotating. Support B moves the strands as it rotates and it moves them from a static position at 0° to a position at 80°. D is an illuminating surface that is placed above the strands. During the movement, pictures are taken which correspond to a known angulation. These pictures have been analysed with Image J software in order to obtain layouts of the luminosity. The reflected light is extrapolated as a peak and its height is measured in pixels. What is measured is the difference of the height of the peaks for each picture. The sum of the differences (DSC—Dynamic Shine Coefficient) is a value which represents the difference in dynamic shine between strand C1 and C2. If the DSC is positive, the dynamic shine will be in favour of strand C2, and, vice versa, if the DSC is negative, the difference will be in favour of strand C1.

An example of the calculations carried out is as follows:

$C2$ PEAK HEIGHT $C2-C1$ PEAK HEIGHT

The DSC is the sum of all the differences

TABLE 5

Calculations carried out to assess the dynamic shine

| ANGLE OF ROTATION | Height (h) of peak C1 | Height (h) of peak C2 | DIFFERENCE of the heights (C2 − C1) |
|---|---|---|---|
| 10° | hC1(10°) | hC2(10°) | hC2(10°) − hC1(10°) |
| 20° | hC1(20°) | hC2(20°) | hC2(20°) − hC1(20°) |
| 30° | hC1(30°) | hC2(30°) | hC2(30°) − hC1(30°) |
| 40° | hC1(40°) | hC2(40°) | hC2(40°) − hC1(40°) |
| 50° | hC1(50°) | hC2(50°) | hC2(50°) − hC1(50°) |
| 60° | hC1(60°) | hC2(60°) | hC2(60°) − hC1(60°) |
| 70° | hC1(70°) | hC2(70°) | hC2(70°) − hC1(70°) |
| 80° | hC1(80°) | hC2(80°) | hC2(80°) − hC1(80°) |
| DSC | | | Sum of the differences |

Two experiments have been carried out to validate the method. In the first experiment (EX1), two untreated hair strands deriving from the same batch were compared, whereas in the second experiment (EX2) a formula containing silicones, known for their shine-supplying property, was applied.

The shine was assessed both with Image J software as well visually by 5 experts (panelist test).

The expert personnel were asked to provide a value between 0 and 5, where 0 indicates no difference in shine between the 2 strands, whereas 5 indicates that strand C2 is much shinier than C1.

The values obtained are shown below:

TABLE 6

Experiment 1 for method validation

| | Sum of the heights of C1 (no treatment) | Sum of the heights of C2 (no treatment) | DSC | Average of the panellist test results |
|---|---|---|---|---|
| EX1 | 3105 | 3152 | 47 | 0 |

TABLE 7

Experiment 2 for method validation

| | Sum of the heights of C1 (no treatment) | Sum of the heights of C2 (no treatment) | DSC | Average of the panellist test results |
|---|---|---|---|---|
| EX2 | 3200 | 4125 | 925 | 4 |

For the purposes of assessing the composition which is the subject matter of the invention, 3 experiments were carried out. The test sequence is shown in Table 8. The treatments were carried out by mixing 10 g of dye with 20 g of activator F1, the mixture was applied on the hair strands and left to settle for 20 minutes. It was subsequently rinsed and the strands were dried.

TABLE 8

Dynamic shine tests carried out with formulas F5*, F6 and F7

| EXPERIMENT | Formula applied to STRAND C1 | Formula applied to STRAND C2 | DSC |
|---|---|---|---|
| EX3 | F5* | F6 | −231 |
| EX4 | F6 | F7 | −100 |
| EX5 | F7 | F5* | 400 |

As can be observed from Table 8, the DSC values are always in favour of formulation F5*, which is the subject matter of the invention. The results show how the composition, in conformity with the invention, provides an improvement in terms of shine when compared to the common ammonia-free dyes that are on the market (F7). Moreover, they surprisingly highlight a synergistic effect of the arginine with the PEG-90 Glyceryl Isostearate (F5* versus F6)

Example 2

Combability

The combability test consists in the use of a DIA-STRON MTT175 dynamometer to assess the work carried out to comb the strands of hair. The hair used in this test is bleached hair, which is notoriously difficult to comb because it is damaged. For this purpose, compositions F8*, F9 and F10 were individually mixed with composition F2 in a 1:1.5 ratio and applied on the bleached strands. The colour development time was 25 minutes at a temperature of 30° C. The strands were rinsed, dried and combed by means of a specific dynamometer.

The test results are shown in Table 9. The percentage reduction indicates a decrease of the amount of combing work due to less friction of the comb on the hair fibres. Therefore, the greater the reduction percentage, the greater the combability.

TABLE 9

Analysis of the combability with the dynamometer:

| Formulation applied to the bleached hair | % reduction in comparison to the bleached hair |
|---|---|
| F8* | 32% |
| F9 | 28% |
| F10 | 15% |
| F11 | 17% |
| F13* | 30% |

The data shows that the dye in conformity with the invention (F8*) has a better cosmetic effect, leaving the hair more manageable and combable, in comparison to formula F10, which represents an ordinary ammonia-free dye widely available on the market. Here too, surprisingly, a synergistic effect of the arginine with the PEG-90 Glyceryl Isostearate (formula F8* versus F9) is found, a synergy which is not present between the PEG-90 Glyceryl Isostearate and the MEA (formula F8* versus F11). Likewise, when PEG-30 glyceryl triisostearate is used in combination with lysine (formula F13*), according to the invention, a greater reduction is obtained when compared to the other formulas not in conformity with the invention.

Example 3

Tensile Properties

In order to assess the tensile properties of the hair, a DIAS-TRON MTT670 dynamometer was used. The assessment was carried out on strands of natural blond hair, which were dyed using the F5*, F6 and F7 formulations mixed with the activator F3 in a ratio of 1:2. The mixture was applied to the strands, and left to settle for 20 minutes. Subsequently, the strands were rinsed, dried and placed on the dynamometer for the measurement of the tensile properties.

The modulus of elasticity (Young's Modulus) is the reference parameter. The greater this parameter is, the better the health (elasticity) of the hair is. Table 10 shows the percentage values obtained when compared to the hair that did not undergo any treatment.

TABLE 10

Analysis of elasticity with the dynamometer

| Formula | % variation of modulus of elasticity |
|---|---|
| F5 | 15% |
| F6 | 5% |
| F7 | −13% |

This example shows how the F5* formulation in conformity with the invention is surprisingly capable of improving the tensile properties of the hair, making it more elastic. This test also shows the synergistic effect of the arginine with the PEG-90 Glyceryl Isostearate (formula F5* versus F6). The ordinary ammonia-free dyes available on the market instead damage the hair making them less elastic and therefore more fragile.

Example 4

Resistance of the Colour to Washing

In order to assess the resistance of the colour to washing, a Konica Minolta colourimeter was used.

In the CIELAB colour space, L* indicates the luminosity whereas a* and b* are the chromaticity coordinates. a* and b* indicate the direction of the colour, +a* is the direction of the red, −a* is the direction of the green, +b* is the direction of the yellow and −b* is the direction of the blue.

The differences of colour can be expressed by the ΔE values, which are defined by the following equation:

$$\Delta E=[(\Delta L^*)^2+(\Delta a^*)^2+(\Delta b^*)^2]^{1/2}$$

The lower the value of ΔE, the lesser the loss of colour after the washings.

For this example, the formulas F5*, F6 and F7 were used, mixed with the activator F4 with a dilution ratio of 1:2. The mixture was applied on the bleached strands, and left to settle for 30 minutes. Subsequently the strands were rinsed, dried and measured with the colourimeter. Then the strands were washed for 10 consecutive times with Alfaparf Linea Salone shampoo, dried and measured again with the colourimeter.

Table 11 shows the data that were obtained for ΔE.

TABLE 11

Loss of colour with the washings

| Formula | ΔE |
|---|---|
| F5* | −14% |
| F6 | −18% |
| F7 | −25% |

The F5* formulation is surprisingly the one which best resists 10 washings.

Example 5

Resistance of the Colour to Light

For the assessment of the resistance of the colour to light, an ATLAS SUN TEST CPS+ was used. The treatments were carried out on bleached strands in the following manner:
- formulas F8*, F9 and F10 were individually mixed with the activator F3,
- The mixture was applied to the bleached strands and left to settle for 30 minutes,
- The strands were rinsed and dried
- The strands were measured with the colourimeter
- The strands were exposed to the SUN TEST for 100000 KJ
- The strands were then again measured with the colourimeter.

Table 12 shows the values obtained for ΔE after exposure to the sun test.

In Table 12. Sun test results:

| Formula | ΔE |
|---|---|
| F8* | −8% |
| F9 | −13% |
| F10 | −14% |
| F11 | −11% |

Formula F8*, in conformity with the invention, is the one that best resists sunlight exposure.

Example 6

Progressive Dye

The progressive dyes are used to gradually colour hair. They are applied directly to the hair and, by means of the reaction with the oxygen present in the environmental air, they slowly dye the hair. Therefore, repeated applications (multiple times a week) are necessary in order to achieve the desired colour.

The F5*, F6 and F7 formulations were applied on hair for 5 minutes and subsequently rinsed and then the strands were dried. The cycle was repeated 5 times, obtaining a darker colour (value measured, L) with each application. The lower the L value, the darker the colour.

The results are shown in Table 13 below.

TABLE 13

| Formula | 1 application | 2 applications | 3 applications | 4 applications | 5 applications |
|---|---|---|---|---|---|
| F5* | 59.25 | 57.45 | 55.32 | 54.21 | 53.68 |
| F6 | 62.12 | 58.2 | 56.01 | 54.81 | 54.12 |
| F7 | 65.23 | 63.42 | 62.15 | 57.56 | 56.45 |

Table 13 shows how the F5* formulation is capable of providing darker colours with each subsequent application, therefore it requires fewer applications to achieve the desired colour.

Example 7

Rheology

For the rheological assessment, a Brookfield R/S PLUS Rheometer was used with a C50-1 probe at a speed of 30 revolutions per minute for 1 minute. Table 14 shows the data obtained for the mixtures F5*, F6 and F7 in combination with the activator F3 in a ratio of 1:2 after 1 second and after 60 seconds. The greater the viscosity at 1 second and after 60 seconds, the better the resistance of the dye to drip from the brush during the transfer of the mixture from the bowl to the hair and the better it will hold on the head during the developing time of the dye.

The results are shown in Table 14 below.

TABLE 14

Viscosity values obtained with the Rheometer.

| FORMULA | Viscosity (Paxs) at 1 second | Viscosity (Paxs) at 60 seconds |
|---|---|---|
| F5* | 1.45 | 0.82 |
| F6 | 0.38 | 0.34 |
| F7 | 0.35 | 0.32 |

F5* has the greatest viscosity at 1 second and after 60 seconds.

The invention claimed is:

1. A composition for colouring keratin fibres comprising:
   a) an alkalinising agent consisting of at least one amino acid having a pKa of greater than 10.00 and at least one ester of a fatty acid and glycerol polyethoxylate; and
   b) at least one oxidation colourant,
   wherein said composition does not contain further alkalinising agents.

2. The composition of claim 1, wherein said amino acid is selected from the group consisting of arginine, lysine, tyrosine and proline.

3. The composition of claim 1, wherein said ester of fatty acid and glycerol polyethoxylate has a mean ethoxylation number of from 5 to 200 and the fatty acid residue has a saturated or unsaturated, linear or branched carbon chain having between 8 and 22 carbon atoms.

4. The composition of claim 3, wherein said ester is can be a monoester, a diester or a triester.

5. The composition of claim 1, wherein said ester is selected from the group consisting of Peg-90 glyceryl isostearate, Peg-30 glyceryl triisostearate, Peg-9 glyceryl laurate and Peg-8 glyceryl trilaurate.

6. The composition of claim 1, wherein said amino acid is arginine and said ester is PEG-90 glyceryl isostearate.

7. The composition of claim 1, wherein said oxidation colorant comprises:
(a) an oxidation colorant selected from the group consisting of 1-acetoxy-2-methylnaphthalene, 5-amino-4-chloro-o-cresol, 4-amino-m-cresol, 6-amino-m-cresol, 3-amino-2,4-dichlorophenol, 6-amino-2,4-dichloro-m-cresol, 3-amino-2,4-dichlorophenol, 5-amino-2,6-dimethoxy-3-hydroxypyridine, 5-amino-2,6-dimethoxy-3-hydroxypyridine, 3-amino-2,6-dimethylphenol, 2-amino-5-ethylphenol, 5-amino-4-fluoro-2-methylphenol sulphate, 2-amino-4-hydroxy-ethylaminoanisole, 2-amino-4-hydroxyethylaminoanisole, 2-amino-3-hydroxypyridine, 4-amino-2-hydroxytoluene, 2-aminomethyl-p-aminophenol, 4-amino-2-nitrodiphenylamine-2'-carboxylic acid, m-aminophenol, o-aminophenol, p-aminophenol, 1,3-bis-(2,4-diaminophenoxy)propane, 4,6-bis(2-hydroxyethoxy)-m-phenylenediamine, 2,6-bis(2-hydroxyethoxy)-3,5-pyridinediamine, N,N-bis(2-hydroxyethyl)-p-phenylenediamine, 4-chloro-2-aminophenol, 2-chloro-p-phenylenediamine, 4-chlororesorcinol, N-cyclopentyl-m-aminophenol, 3,4-diaminobenzoic acid, 4,5-diamino-1-((4-chlorophenyl)methyl)-1H-pyrazole-sulphate, 2,3-diaminodihydropyrazolo pyrazolone dimethosulphonate, 2,4-diaminodiphenylamine, 4,4'-diaminodiphenylamine, 2,4-diamino-5-methylphenetole, 2,4-diamino-5-methylphenoxyethanol, 4,5-diamino-1-methylpyrazole, 2,4-diaminophenol, 2,4-diaminophenoxyethanol, 2,6-diaminopyridine, 2,6-diamino-3-((pyridin-3-yl)azo)pyridine, N,N-diethyl-m-aminophenol, N,N-diethyl-p-phenylenediamine, N,N-diethyltoluene-2,5-diamine, 2,6-dihydroxy-3,4-dimethylpyridine, 2,6-dihydroxyethylaminotoluene, dihydroxyindole, dihydroxyindoline, 2,6-dimethoxy-3,5-pyridinediamine, m-dimethylaminophenyl urea, N,N-dimethyl-p-phenylenediamine, 2,6-dimethyl-p-phenylenediamine, N,N-dimethyl 2,6-pyridinediamine, 4-ethoxy-m-phenylenediamine, 3-ethylamino-p-cresol, 4-fluoro-6-methyl-m-phenylenediamine, 1-hexyl 4,5-diamino pyrazole sulphate, hydroquinone, hydroxyanthraquinoneaminopropyl methyl morpholinium methosulphate, hydroxybenzomorpholine, hydroxyethoxy aminopyrazolopyridine, hydroxyethylaminomethyl-p-aminophenol, 1-hydroxyethyl 4,5-diamino pyrazole, hydroxyethyl-2,6-dinitro-p-anisidine, hydroxyethyl-3,4-methylenedioxyaniline, hydroxyethyl-p-phenylenediamine, 2-hydroxyethyl picramic acid, 6-hydroxyindole, hydroxypropyl bis(N-hydroxyethyl-p-phenylenediamine), hydroxypropyl-p-phenylenediamine, hydroxypyridinone, isatin, N-isopropyl 4,5-diamino pyrazole, N-methoxyethyl-p-phenylenediamine, 6-methoxy-2-methylamino-3-aminopyridine, 2-methoxymethyl-p-aminophenol, 2-methoxymethyl-p-phenylenediamine, 2-methoxy-p-phenylenediamine, 6-methoxy-2,3-pyridinediamine, 4-methoxytoluene-2,5-diamine, p-methylaminophenol, 4-methylbenzyl 4,5-diamino pyrazole, 2,2'-methylenebis 4-aminophenol, 3,4-methylenedioxyaniline, 3,4-methylenedioxyphenol, 2-methyl-5-hydroxyethylaminophenol, methylimidazoliumpropyl p-phenylenediamine, 2-methyl-1-naphthol, 2-methylresorcinol, 1,5-naphthalenediol, 1,7-naphthalenediol, 2,3-naphthalenediol, 2,7-naphthalenediol, 1-naphthol, 2-naphthol, PEG-3 2,2'-di-p-phenylenediamine, p-phenetidine, m-phenylenediamine, p-phenylenediamine, phenyl methyl pyrazolone, N-phenyl-p-phenylenediamine, picramic acid, pyrocatechol, pyrogallol, resorcinol, sodium picramate, tetraaminopyrimidine, tetrahydro-6-nitroquinoxaline, tetrahydropyranyl, resorcinol, toluene-2,5-diamine, toluene-2,6-diamine, toluene-3,4-diamine, 2,5,6-triamino-4-pyrimidinol, and 1,2,4-trihydroxybenzene, or
(b) a cosmetically acceptable salt of an oxidation colorant of (a).

8. The composition of claim 1, further comprising a neutralising agent.

9. The composition of claim 8, wherein said neutralising agent comprises a sodium hydroxide, potassium hydroxide, urea, allantoin, tripotassium phosphate, sodium saccharin or a combination thereof,
wherein said neutralising agent is present in at least an amount sufficient to neutralise acidic ingredients present in the dye.

10. The composition of claim 1, in a form selected from the group consisting of oil-in-water emulsion (O/W), water-in-oil emulsion (W/O), biphasic liquid, gel, oil, aerosol and mousse.

11. A Ready-to-use composition for colouring hair, comprising: (a) a composition of claim 1; and (b) an activator.

12. A Kit for colouring hair, comprising a composition of claim 1 and an activator.

13. The Kit of claim 12, wherein said activator is present in an amount of between 0.1 and 50 wt. % of the final dye.

14. A Method for dying a hair, comprising the following steps:
(a) mixing the composition of claim 1 with an oxidative solution;
(b) subsequently applying it to the hair;
(c) subsequently rinsing it off; and (d) drying the hair.

15. A Method for dying a hair, comprising: applying the composition of claim 1 to the hair;
wherein optionally the method further comprises subsequently rinsing the hair off; and optionally the method further comprises drying the hair.

16. The composition of claim 1, wherein the keratin fibres are human hair keratin fibres.

17. The composition of claim 1, wherein the composition does not contain ammonia or an alkanolamine.

18. The composition of claim 1, wherein the composition further comprises: an aliphatic mono or poly-alcohol with low molecular weight, or an ester or ether thereof; an emulsifier; a wetting agent, a surfactant, a thickener; a conditioning agent; an electrolyte; an antioxidant; a protein derivative, a provitamin, a vitamin, a plant extract, sugar, betaine, a fatty amide, a sequestrant, a film-forming agent, a preservative or a combination thereof.

19. The method of claim 14, further comprising washing the hair with shampoo before drying the hair.

20. A composition for colouring keratin fibres comprising:
a) an alkalinising agent consisting of at least one amino acid having a pKa of greater than 10.00 and at least one ester of a fatty acid and glycerol polyethoxylate; and
b) at least one oxidation colourant, wherein said composition does not contain further alkalinising agents,
wherein said ester is selected from the group consisting of Peg-90 glyceryl isostearate, Peg-30 glyceryl triisostearate, Peg-9 glyceryl laurate and Peg-8 glyceryl trilaurate.

21. A composition for colouring keratin fibres comprising:
a) an alkalinising agent consisting of at least one amino acid having a pKa of greater than 10.00 and at least one ester of a fatty acid and glycerol polyethoxylate; and
b) at least one oxidation colourant, wherein said composition does not contain further alkalinising agents,
wherein said at least one amino acid comprises an arginine and said ester is PEG-90 glyceryl isostearate.

* * * * *